United States Patent [19]

Kiesewetter et al.

[11] Patent Number: 4,554,821
[45] Date of Patent: Nov. 26, 1985

[54] APPARATUS FOR DETERMINING THE VISCOSITY OF FLUIDS, IN PARTICULAR BLOOD PLASMA

[76] Inventors: Holger Kiesewetter; Friedrich Jung, both of Stockwiese 44, 6650 Homburg-Kirrberg; Hans-Günther Roggenkamp, Kullenhofstr. 36, 5100 Aachen, all of Fed. Rep. of Germany

[21] Appl. No.: 522,203

[22] Filed: Aug. 11, 1983

[30] Foreign Application Priority Data

Aug. 13, 1982 [DE] Fed. Rep. of Germany ....... 3230246

[51] Int. Cl.⁴ ............................................. G01N 11/04
[52] U.S. Cl. ............................................. 73/55; 73/54
[58] Field of Search .................... 422/82, 99; 128/DIG. 13; 73/55, 54, 57

[56] References Cited

U.S. PATENT DOCUMENTS

| | | | |
|---|---|---|---|
| 2,065,695 | 12/1936 | Haultain | 73/55 |
| 2,625,817 | 1/1953 | Oppenauer | 73/54 |
| 3,713,328 | 1/1973 | Aritomi | 73/55 |
| 3,924,448 | 12/1975 | Howard et al. | 73/55 |
| 4,135,509 | 1/1979 | Shannon | 128/DIG. 13 |
| 4,137,940 | 2/1979 | Faisandier | 128/DIG. 13 |
| 4,346,606 | 8/1982 | Cannon et al. | 128/DIG. 13 |

Primary Examiner—Stewart J. Levy
Assistant Examiner—Hezron E. Williams
Attorney, Agent, or Firm—Finnegan, Henderson, Farabow, Garrett & Dunner

[57] ABSTRACT

An apparatus for determining the viscosity of fluids, particularly blood plasma, includes an outer housing including a front surface having a groove therein; a disposable capillary tube removably mounted in the groove and including at least one loop, each of the loops having two substantially horizontal branches including an upper branch and a lower branch for flowing the fluid under the influence of gravity through a predetermined path, and a device for measuring the rate of flow of the fluid along the path in one of the horizontal branches. Also disclosed is a flexible disposable capillary tube for the fluid viscosity measuring apparatus.

25 Claims, 4 Drawing Figures

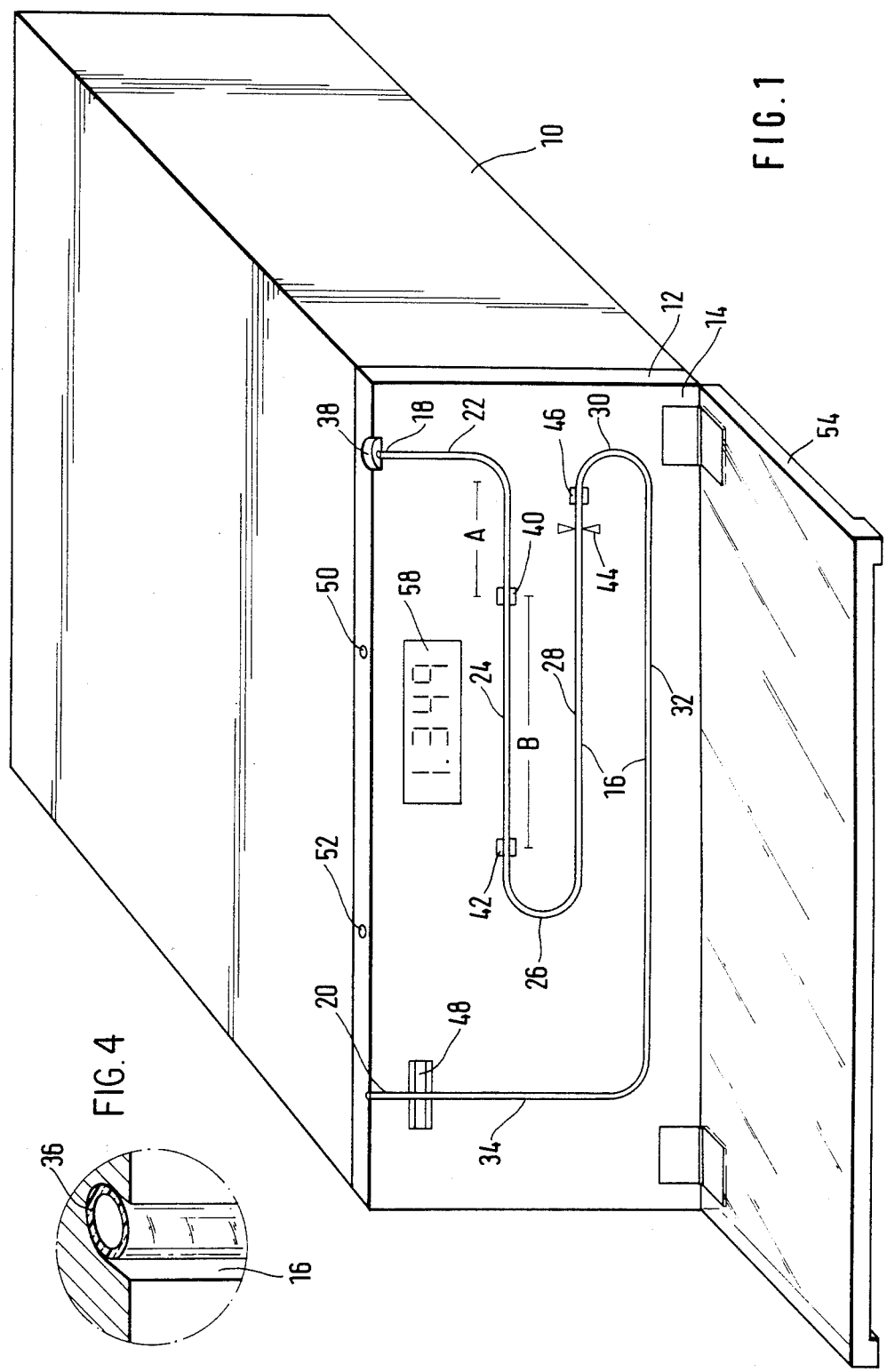

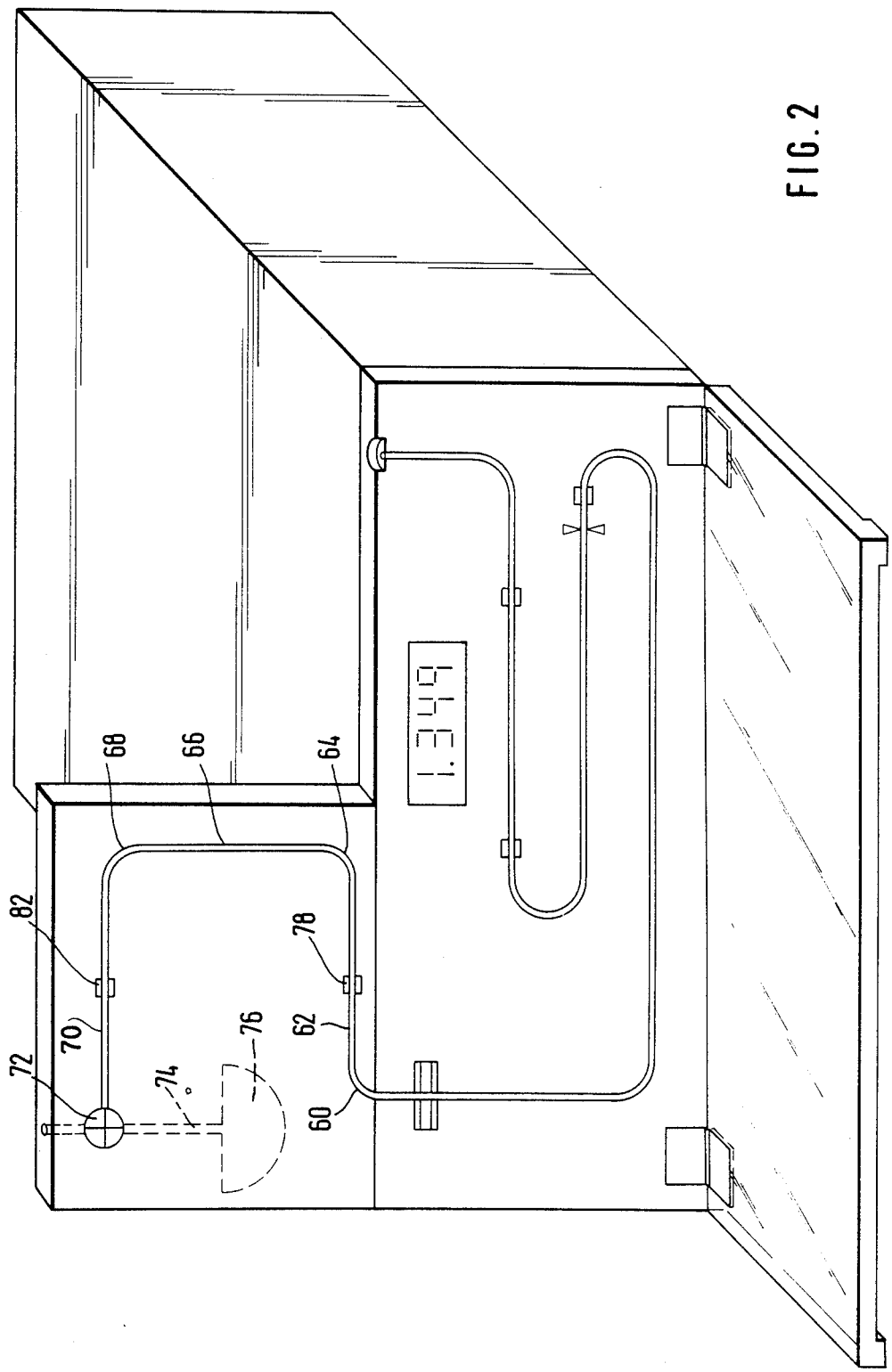

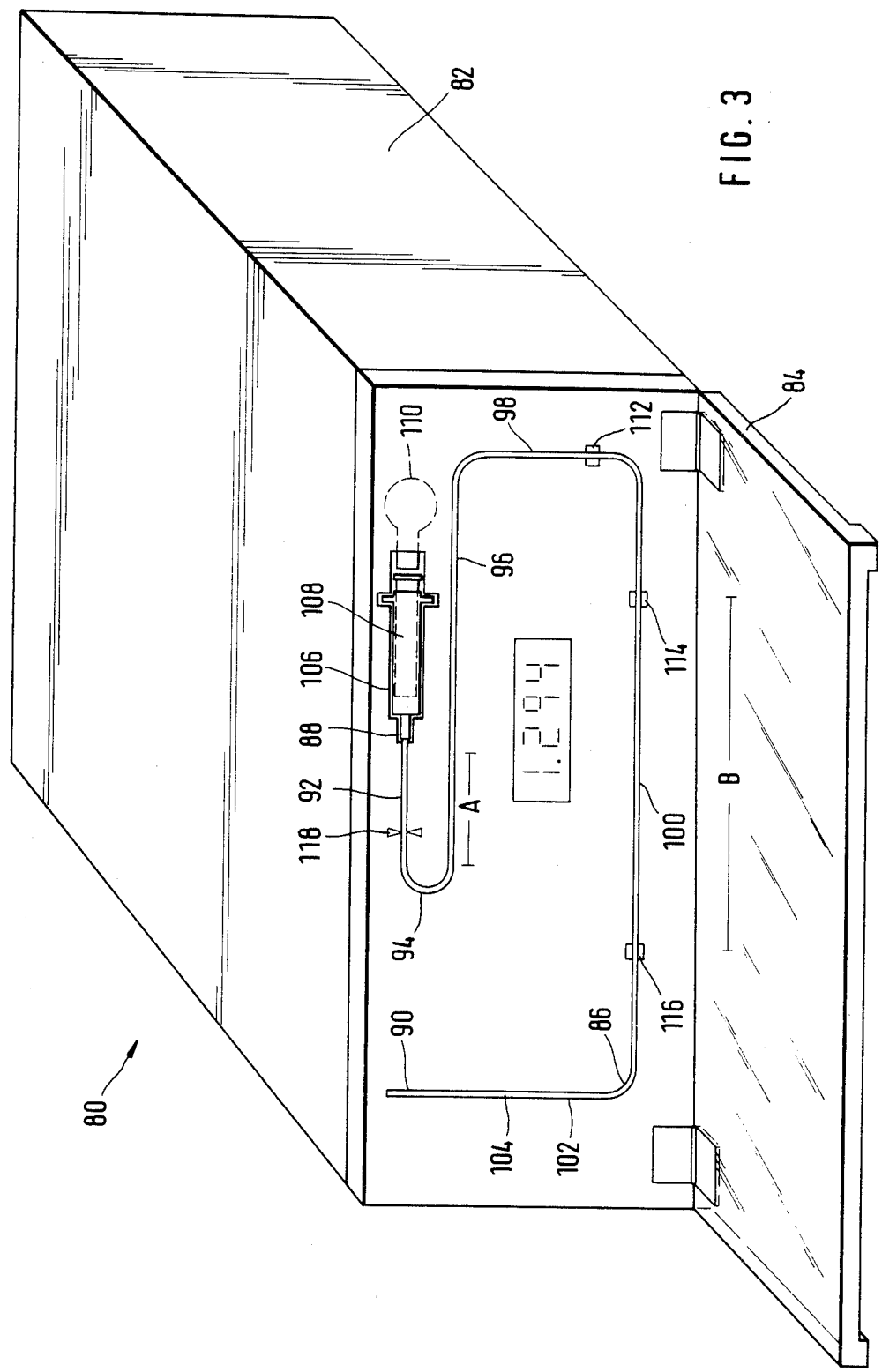

APPARATUS FOR DETERMINING THE VISCOSITY OF FLUIDS, IN PARTICULAR BLOOD PLASMA

The invention relates to an apparatus for determining the viscosity of fluids, in particular blood plasma, which comprises a capillary tube for the passage of the fluid under the influence of gravity and a means for determining the flow through time.

Blood may be regarded as an independent moving organ which is a suspension of various cells in the plasma as continuous phase. Its purpose is essentially to convey the blood cells and the plasma through all parts of the vascular bed. In this plasma there are fats, electrolyte and in particular proteins. By mass and heat transport the blood serves to maintain a so-called flow equilibrium which is adapted to the respective organs and their cells. Thus, an increased energy requirement is met by an increase in the blood flow and thus by an increase in the amount available of oxygen, glucose or fatty acids, whilst at the same time ensuring the carrying away of metabolism intermediate and final products. If for any reasons such a flow equilibrium cannot be maintained over a relatively long time the organism cannot survive.

To maintain this vital flow equilibrium a blood flow $v_{blood}$ adapted to the specific requirements of the organism must be ensured. For each individual vessel this flow can be approximately derived from the Hagen-Poiseuille law:

$$\dot{v}_{blood} = (\Delta p \pi r^4)/(8\, l\, \eta_{blood}) \tag{1}$$

The driving pressure $\Delta p$ depends effectively on the pumping capacity of heart, whilst the full blood viscosity $\eta_{blood}$ and the vascular geometry (l=length, r=vessel radius) fix the hydrodynamic resistance of the flow passage.

The intensive investigation carried out in recent years of the influence of full blood viscosity on the flow behaviour of blood has clearly shown that under pathological conditions it is precisely this quantity which can be the limiting factor for the perfusion.

The apparent viscosity of the blood, which is a non-Newtonian fluid, depends essentially on the following factors: the plasma viscosity, the hematocrit value (volume proportion of the blood cells with respect to the total blood), the aggregation of the erythrocytes and the deformability of the erythrocytes. Each of these factors, i.e. including the plasma viscosity, plays an important part in the recognition of diseases in the blood and consequently there is a need to determine each of these factors as simply and accurately as possible in routine medical practice.

For the quantification of the plasma viscosity essentially the following types of viscosimeters are known: the falling ball, the rotation and the capillary viscosimeters; the measuring instruments used at present are poorly suited to routine medical practice for the reasons explained below.

The design of the falling ball viscosimeter is based on the theory of Stokes according to which the following equation applies for the resistance of a sphere about which there is a flow:

$$F_W = 6\pi \eta_{Pl} r_K v_K \tag{2}$$

After a short starting distance the ball drops in the fluid with constant velocity. The force of gravity on the sphere with the density $\rho K$ is held in equilibrium by the buoyancy and the frictional force $F_W$. From the equation $$4/3\pi(\rho_K - \rho_{Pl})r_K^3 g = 6\pi \eta_{Pl} r_K v_K \tag{3}$$

and the time t which the sphere needs to cover a defined distance l, the mean velocity $v_K = l/t$, the viscosity is obtained as:

$$\eta_{Pl} = 2/9 r_K^2/l\, g(\rho_K - \rho_{Pl})t \tag{4}$$

Usually the expression $2/9\, r_K^2/l\, g$ is incorporated into the experimentally determined apparatus constant K so that the viscosity can be determined empirically.

However, due to the visual timing the measuring inaccuracies with this method are relatively large and can be avoided by opto-electronic steps.

It is also to be remembered that the theory on which this method is based requires maintenance of a creeping flow and thus the use of relatively large spheres. This involves a filling volume of at least 50 ml plasma corresponding to a blood volume of about 100 ml. Such a blood extraction usually represents an unacceptable strain on the patient, particulary when it is necessary to frequently carry out several measurements (measurements of further parameters; therapy supervision).

The second method of determining plasma viscosity is rotation viscosimetry. The plasma viscosity is obtained by the following formula $$\eta_{Pl} = K\, M_D/\Omega, \tag{5}$$

where
  K = apparatus constant,
  $M_D$ = torque and
  $\Omega$ = angular velocity The apparatus constant, which depends on the type of measuring chamber used, involves a large number of sources of error due to the nature and working of the measuring chamber.

Thus, the first group of such viscosimeters consists of an arrangement of coaxial cylinders, for example the GDM-viscosimeter (Gilinson-Dauwalter-Merrill), whilst the second group has a plate-cone arrangement, for example the Wells-Brookfield-viscosimeter.

A frequently employed rotation viscosimeter uses both of said chamber arrangements, i.e. the so-called Mooney-configuration. This involves co-axial cylinders which are formed at the upper and lower side as a plate-cone system. Further forms of chamber geometry are for example the rhombo-spheroid viscosimeter of Dintenfass or the rheogoniometer of Weissenberg.

In most rotation viscosimeters the speed of rotation is predetermined using a transmission gear and the torque delivered is measured, said torque depending on the plasma viscosity. In contrast, the rotation rheometer of Deer (Mooney-configuration) operates with predetermined torque, the speed delivered being measured.

Since the theory of the rotation viscosimeter assumes a stationary shear flow in the annular gap, the inner and outer cylinders must be made very accurately to ensure good reproducibility of the measurements. In addition, the chamber must be carefully cleaned after each measurement and no residues of the cleaning agent must be left in the chamber. Such residues of the test solution and the cleaning agent change the wettability of the surfaces of the measuring chamber and this directly influences the measurement. Moreover, per measurement about 15 ml plasma is required, corresponding to about 30 ml full blood. Since for determining a mean value usually several measurements are carried out, the result is that larger amounts of blood must be taken from the patient, representing an increased strain on him and thus being undesirable.

The best known method for viscosity measurement of plasmas consists in determining the discharge time or the volume flow $\dot{V}$ which is measured in a capillary viscosimeter. For the mean velocity in a capillary, according to Hagen-Poiseuille the following equation applies:

$$\dot{V}_{Pl} = (\Delta p \, r_i^2)/(8\eta_{Pl} l), \quad (6)$$

where $\Delta p$ = pressure loss in the capillary observed,
$r_i$ = internal radius of the capillary and
$l$ = length of the capillary considered.

All types of capillary viscosimeters determine the plasma viscosity on the basis of this law. The mean velocity $\bar{v} = l/t$ is determined by measuring the time which the plasma requires to cover a defined distance l. Since the geometry of capillary ($r_i$, l) is fixed, if $\Delta p$ is known the viscosity can be calculated.

Thus, the capillary viscosimeter of Harkness produces a constant pressure differential $\Delta p$ via a vacuum pump in a horizontally disposed capillary.

Furthermore, a viscosimeter is known from Ubbelohde in which the weight of the plasma column is used as driving pressure.

A further viscosimeter with continuously variable pressure has been developed by Martin et al.

The capillary viscosimeter frequently used in the art according to Ostwald comprises a U-tube capillary with vertically disposed legs and is distinguished by an exactly reproducible measuring volume for likewise exactly adjustable pressures.

Common to all these capillary viscosimeters is that they require a complicated apparatus construction due to the frequently only very short measuring time and the correspondingly necessary detector means. In addition, the capillaries used are difficult to make and consequently, due to manufacturing tolerances, measuring errors occur; furthermore, since they consist of glass, they must be temperature regulated over a longer period of time so that their availability is limited. In addition, the cleaning of such a measuring capillary, as explained above, represents a further disadvantage because it must be carried out very carefully, and only capillaries completely free from residue can be used. Furthermore, with vertically disposed capillaries there is the disadvantage that drop formation may occur at the discharge end, which falsifies the measuring time of the fluid column passing through the capillary due to the opposing surface tension of the drop so that such a capillary must have special adaptor members which are difficult to produce.

The problem underlying the invention is therefore to provide an apparatus of the type mentioned at the beginning with which the viscosity of even rapidly flowing fluids can be exactly and reproducibly determined at relatively short intervals, only very small amounts of fluid being required and complicated cleaning operations being unnecessary.

This problem is solved in that the capillary tube is disposed in at least one loop having two substantially horizontal branches and is arranged in a correspondingly formed groove of a front plate of the apparatus.

The apparatus according to the invention firstly has the advantage that only so-called expendable capillaries can be used, i.e. the capillaries can be cheaply made and thrown away after use. Preferably suitable for this purpose is a flexible plastic tube which can be made with the necessary tolerances. Advantageously such plastic materials substantially do not interact with the fluids to be investigated in the measuring time, i.e. do not pass any plasticizer and the like to the fluid.

Such a flexible tube capillary is disposed in a groove, shaped corresponding to the desired capillary path, of a plate which secures the capillary tube. The preferred capillary path is for the tube to be disposed in at least two loops, the respective loop branches being disposed substantially parallel and horizontal. The loop radius is dimensioned so as to reliably avoid any squeezing or bending of the tube capillary.

The diameter of the capillary is chosen so that the column of fluid to be investigated on passing through the capillary does not break away or cling to the capillary due to surface tension, thus preventing flow. For the latter purpose, the entry end of the capillary is preferably formed as so-called accelerating section and shaped so that from the upper horizontal branch a substantially perpendicular branch is led to the inlet opening. After passing through this accelerating section in which the static friction of the fluid at the start of the measurement in the tube is overcome with certainty, the fluid enters the horizontal branch whose first portion is advantageously formed as preliminary or settling section. After passage of the settling section it is ensured that a stationary flow is present in the tube capillary and can be subjected to the actual measurement.

Due to the measurement section disposed in loops and arranged substantially in a horizontal plane, during the measurement a constant driving pressure differential $\Delta p$ is present, acting over the height difference between the individual horizontally disposed branches. Whereas in the prior art a substantially perpendicular capillary is employed through which the fluid flows in a very short time, in contrast according to the invention a capillary arrangement is provided which consists both of a vertically and of a horizontally disposed portion, both portions being accommodated on a small area. This is achieved in that the tube capillary is disposed in meander form or in oppositely disposed loops. Thus, the flow of a fluid in a substantially horizontal tube and the flow of a fluid in a substantially perpendicular tube are superimposed. As a result the measuring times in such an arrangement are considerably greater than the measuring times in an only vertically disposed measuring section. This of course substantially reduces the measuring errors and the measuring times can be measured far easier and more accurately than with a vertical arrangement.

In a further advantageous embodiment the flexible tube capillary comprises at its end a rise section which prevents the fluid being investigated from flowing out and/or the discharging fluid from forming drops which falsify the measuring times as explained above.

After the measurement the tube is removed from the groove in the plate and is kept for further determinations of the fluid or thrown away. Thus, no discharge effects occur. Furthermore, no cleaning of the capillary is necessary and consequently the negative effects mentioned at the beginning are completely obviated.

A further explanation of the invention is given by the following description of three examples of embodiment with the aid of the drawings, wherein:

FIG. 1 is a schematic front elevation of a first embodiment of the apparatus according to the invention, FIG. 2 is a schematic front elevation of a second embodiment of the apparatus according to the invention, FIG. 3 is a schematic front elevation of a further embodiment which is substantially similar to the apparatus shown in FIG. 1, and FIG. 4 is an enlarged view of capillary tube mounted in the groove.

The first embodiment shown in FIG. 1 consists essentially of a housing 10 which has an inclined or preferably vertical front plate 12. Disposed in said housing 10 is the electronic control means and the like.

Worked into the front side 14 of the front plate is a groove 16 which extends from an inlet end 18 to an outlet end 20.

In the embodiment shown in FIG. 1 the groove extends from the inlet end 18 into a substantially vertically disposed branch 22 which serves as acceleration section.

This branch 22 is adjoined by a first horizontal branch 24, which is divided into a settling section denoted by A and a measuring section denoted by B.

This branch 24 is disposed in a loop 26 which is continued in a branch 28 which once again is advantageously disposed horizontally.

In the embodiment shown in particular in FIG. 1 the branch 28 is followed by a second loop 30 which is again continued in a substantially horizontally disposed branch 32. This branch 32 is considerably longer than the branches 24 and 28 and advantageously so dimensioned that its length corresponds substantially to the length of the branches 22, 24 and 28 and of the loop 26.

According to a preferred embodiment the branch 32 is followed by a branch 34 arranged substantially as rise section and led back to the outlet end 20.

It is pointed out that of course the branches 22 and 34 are only present in a preferred embodiment, i.e. that the branches 24 and 32 can also terminate substantially horizontally in the inlet and outlet ends.

Furthermore, the embodiment shown in FIG. 1 is of course not restricted to an arrangement of two loops 26 and 30. On the contrary, it may have only one loop 26 so that the branch 28 itself represents the outlet branch. This embodiment is, however, less preferable because the length of the groove resulting from the reduction in size of the apparatus, is not always adequate for an effective measurement of the viscosity.

The groove 16 is sized so that a flexible tube 36 can be fitted exactly therein, as apparent from the enlarged perspective section shown in FIG. 1.

The tube 36 runs from the inlet end 18 to the outlet end 20 in exact fit in the groove 16 in such a manner that no bends or constrictions occur therein, i.e. the cross-section of the tube remains substantially constant over the entire length thereof.

Thus, the depth and width of the groove 36 corresponds substantially to the tube diameter. It has been found advantageous for the flexible tube to have a substantially circular cross-section, the internal diameter being about 0.5–2 mm, preferably about 0.7–1.0 mm.

To obtain the best possible temperature compensation with the advantageously temperature controlled front plate 12, as explained below, the wall thickness of the flexible tube is about 0.2–0.5 mm, preferably 0.3–0.4 mm.

As tube material, a transparent plastic material is used which is light-permeable so that the fluid fronts occurring in the tube can be detected by means of optical sensors. As preferred plastic material polyurethane and polyethylene are used, being substantially free from plasticizers. Particularly preferable is polyurethane which can be supplied in the desired tolerances and gives highly reproducible measuring results.

For the exact insertion of the tube into the groove 16 a bead may be provided at the beginning thereof which can be inserted into a recess 38 in the front plate 12 in the region of the inlet end 18. This permits both exact insertion of the tube and also facilitates filling of the test fluid into the tube.

Provided in the front plate 12 in the region of the branch 24 of the groove 16 are two detectors 40 and 42 which are preferably in the form of light sensors. Advantageously, said light sensors are inserted in each case in an opening provided in the branch 24 and do not restrict the insertion of the tube 36 into said branch 24. These sensors 40 and 42 are sensitive so that they respond to the occurrence of a fluid meniscus and the resulting light change.

Downstream of the sensor 42 in the branch 28 is a filling mark 44 in the immediate vicinity downstream of which is provided a further sensor 46. Said sensor 46 corresponds in type and construction and arrangement to the sensors 40 and 42. Said sensor 46 controls via an electrical circuit, not illustrated, a closure magnet 48, which is arranged in the vicinity of the outlet end 20.

On occurrence of a signal at the sensor 46 the closure magnet 48 is activated and closes the tube 36 inserted in the groove 16 for a predetermined time, preferably about 0.5–4 Min., in particular 1–2 Min. This time serves to bring the fluid present in the tube 36 to the temperature in the front plate 12 and correspondingly in the tube 36, representing a dry temperature regulation.

For the temperature regulation the front plate 12 is provided with two terminals 50 and 52 which are constructed as electrical terminals or as tube terminals for supplying a correspondingly heated fluid originating from a reservoir which is not illustrated. The preferable arrangement is an electrical heating by means of a heating coil, not illustrated, which is provided in the front plate 12 and connected to the terminals 50 and 52. Said terminals 50 and 52 may of course also be accommodated within the housing 10. If it is intended to measure the viscosity of blood plasma, the front plate 12 and thus the tube 36 are brought to the body temperature, i.e. about 37° C. When using other fluids, of course, any desired temperatures can be adjusted in the front plate, which consists preferably of aluminium.

Furthermore, the front plate 12 comprises at its lower end a preferably pivotable cover 54 advantageously made from a transparent plastic material. On closing the cover the display 58 can be erased so that a new value can be measured.

With the apparatus according to the invention the viscosity is measured according to the following rules and in the following manner:

The time t which the fluid, in particular blood plasma, requires to cover the defined measuring section B in the tube 36 is measured.

Assuming a Hagen-Poiseuille flow in the capillary, the volume flow is represented by the following equation $$\dot{V}_{Pl} = (\pi r_s^4 \Delta p)/(8\eta_{Pl} l), \qquad (7)$$

wherein $\dot{V}_{Pl}$ = plasma volume flow, $r_s$ = radius of the capillary tube, $l$ = length of the plasma column and $\eta_{Pl}$ = dynamic viscosity of the plasma.

With $\dot{V} = V/t$ and $V = \pi r^2 l_M$ the dynamic viscosity is obtained from the equation:

$$\eta_{Pl} = (\Delta p\, r_s^2 t)/(8\, l\, l_M), \qquad (8)$$

wherein $l$ = length of the measuring section (B) and $t$ = measured flow-through time.

The driving pressure $\Delta p$ is the hydrostatic pressure of the plasma column defined purely geometrically by the difference in height of the measuring section with respect to the branch 32. Consequently, the equation for determining the dynamic viscosity $\eta_{Pl}$ is:

$$\eta_{Pl} = (g\, r_s^2 \Delta h\, \rho_{Pl} t)/(8\, l\, l_M), \qquad (9)$$

wherein g = acceleration due to gravity, h = the driving height difference fixed by the design and $\rho_{Pl}$ = density of the plasma.

All the constants are combined to give an apparatus constant K. Thus:

$$\eta_{Pl} = K\, f_{Pl}\, t \qquad (10)$$

It is apparent from this formula that the kinematic viscosity $\nu_{Pl} = \eta_{Pl}/\rho_{Pl}$ can be obtained directly by measuring the flow time. Since the density of the plasma fluctuates only within narrow limits (max $\pm 3\%$), in a simple embodiment assuming a mean plasma density $\bar{f}_{Pl}$ the dynamic viscosity can also be calculated by the following formula (11) and emitted as value:

$$\eta_{Pl} = K\, \bar{f}_{Pl}\, t$$

The measuring error possible by this simplifying assumption is certainly less than $\pm 3\%$.

For carrying out the measurement the tube 36 is first inserted into the groove 16 of the front plate 12. Thereafter, the fluid to be investigated, in particular plasma obtained from the anticoagulated blood taken from the patient, is introduced into the tube in an amount of about 200–400, max. 500 μl. For this purpose, a 2 ml syringe is preferably used, the cannula of which is introduced into the capillary of the tube 36. This cannula seals the capillary so that the fluid advances in the capillary only by the pressure on the plunger of syringe. The filling of the capillary is completed when the fluid front reaches the filling mark 44.

Thereafter, either the syringe cannula is left in the capillary until the liquid introduced is heated to the temperature of the front plate 12, or preferably the cannula is removed after the filling so that the fluid front advances up to the sensor 46. The sensor 46 is thereby actuated and again activates the closure magnet 48 which squeezes the tube 36 so that the fluid column can no longer advance in the tube 36.

For a predetermined time of about 0.4–4 Min., especially 1–2 Min., the temperature regulation is carried out and thus a dry temperature control of the preferably used plasma to about 37° C. After this time the closure magnet 48 opens automatically and the actual measuring operation begins.

The branch 22 first serves as an acceleration path in which the static friction of the fluid in the tube 36 is overcome. Thereafter, the fluid enters the settling section A of the branch 24 in which a substantially stationary flow is achieved. On passing the first sensor 40, i.e. entering the measuring section B, the measuring operation is started and is completed when the forward edge of the fluid has reached the second sensor 42. The time measured is then shown on the display 58 and corresponds to a viscosity value which can be read from a calibration curve After passage through the measuring section B the flow of the fluid continues in the lower branch 32 until it is retarded by the rise in the branch 34 and brought to a stop.

Thereafter, the cover 34 closing the front plate 12 during the measurement is opened and the flexible tube 36 removed from the groove 16. The plasma contained in the tube can either be used again or discarded together with the tube 36. For the measurement of blood plasma it has been found particularly advantageous for the measuring section B to be about 30–200 mm, in particular about 80–120 mm long, and the geometrically defined driving height, i.e. the vertical distance between the branch 24 and the branch 32, to be about 40–160, in particular 90–120 mm long.

The apparatus may of course also have a programmed calibration curve so that the display 58 automatically shows the viscosity value calculated. This display is advantageously left until the next measurement.

For each further measurement a new capillary tube is used. This eliminates all the otherwise necessary cleaning operations and because of the wettability, which is the same in each case, guarantees excellently reproducible measurements with an error range of max. $\pm 2\%$.

Since the apparatus is very handy, its setting up, insertion and filling of the tube, takes at the most about 1 Min. Advantageously, all the subsequent measuring operations, including the preliminary temperature regulation of the plasma, take place automatically and do not require any special attention or presence. Thus, the apparatus is available again for a measurement about every 2–3 Min.; because of its small dimensions, its dry temperature regulation and its simple time-saving manipulation, the apparatus is portable and can thus for example be used directly for bed-side diagnosis. After a short explanation it can be used without error by any non-skilled person and requires no cleaning operations whatever so that any number of measurements can be carried out in a short period of time. Since only a very small measuring volume (max. 200 μl) is required, the apparatus can be used for daily therapy supervision without putting an excessive strain on the patient.

A further embodiment is illustrated in FIG. 2 in which identical reference numerals represent identical parts. The apparatus shown in FIG. 2 permits the determination of the dynamic and kinematic viscosity because this apparatus is additionally equipped with a density measuring means.

As apparent from FIG. 2, this apparatus comprises in its right-side region the apparatus described above for determining the viscosity so that the latter need not be explained again in detail. Compared with the embodiment shown in FIG. 1, the branch 34 branches off at 60 again into a lower substantially horizontal branch 62.

The branch 62 is again disposed in a bend 64 which is followed by a vertical branch 66. Via a bend 68 this branch is connected with a further substantially horizontal branch 70 comprising a three-way shut-off member disposed laterally at the front plate 12. This three-way shut-off member 72 can however also be accommodated in the housing 10, the tube 36 being correspondingly connected thereto.

Thus, the groove 16 and the tube 36 extend in this second embodiment up to the three-way shut-off member 72, which either frees the tube 36 for ventilation or establishes a fluid connection to a suction pump 76 via a conduit 74. During the viscosity measurement outlined above this three-way shut-off member 72 is set to "vent".

If however the density of the fluid is to be measured after the viscosity value has been determined, the three-way shut-off member 72 is automatically switched and the connection to the suction pump 76 established.

The density is measured in the following manner:

A partial vacuum is applied to the plasma column in the tube 36 and lifts said column in the left portion of the measuring arrangement, i.e. in the branches 34, 62, 66 and 70. With increasing height an increasing vacuum is necessary and this is supplied by the suction pump 76. To ensure a reliable measurement the driving height defined by the vertical distance between the branches 62 and 70 is made considerably greater than the driving height employed in the viscosity measurement. It is for example about 60–120, especially 80–100 mm.

Firstly, the fluid column disposed in the branch 34 is sucked by the partial vacuum into the branch 62 in which a sensor 78 is disposed which is constructed preferably as an optoelectronic sensor. This sensor 78 serves to determine a first pressure value $p_1$ which is either shown on the display 58 or stored in a corresponding electronic retaining circuit. Thereafter, the fluid is drawn with increased vacuum into the upper branch 70 in which, once again, a sensor 82 is disposed which has the same form as the sensor 78 mentioned above. Preferably, these sensors 78 and 82 correspond to the sensors 40–42 and 46.

The second value $p_2$ measured at the sensor 82 is also found and the difference between these values gives the desired density $\rho$ according to the equation (12)

$$p_1 - p_2 = \rho g(h_1 - h_2)$$

The advantage of the greater driving height is the substantial reduction in the influence of the wettability of the tube 36, which in any case cancels itself out in the aforementioned difference formation. The height $h_1 - h_2$ represents in each case the distance of the branch 62 and 70 respectively from the meniscus of the fluid disposed in the branch 34.

This meniscus height is defined by the overall arrangement of the tube, and the introduction of the fluid up to the filling mark.

In a further embodiment corresponding substantially to FIG. 1 the outlet end 20 is connected to the three-way shut-off member 72 which is connected to an excess pressure pump, not illustrated. In this density measurement the fluid column is driven back into the branch 28 and 24 by excess pressure, the sensors 46, 42 and 40 being used to determine the pressure values $p_1$ and $p_2$ respectively. However, this embodiment is not preferable to the embodiment described above.

By the determination of the density $\rho_{Pl}$ and the aforementioned dynamic viscosity, the equation $$\nu_{Pl} = \eta_{Pl}/\rho_{Pl} \tag{13}$$

can be applied and consequently the most important rheological parameters of a fluid can be determined in a simple apparatus which is easy to operate. Thus, apart from determining the viscosity, by means of only one measurement of the plasma density, direct information on the total protein content in the plasma can be obtained.

A comparison of the plasma viscosities obtained with the calibration curve shows that the values correspond very well to the values obtained with a Coulter-Harkness viscosimeter. The deviations of the values are about ±0.5%.

In FIG. 3, 80 denotes a further particularly preferred embodiment of a viscosimeter according to the invention, this embodiment being substantially similar to that shown in FIG. 1. In this respect reference is made to the above remarks on FIG. 1.

The viscosimeter 80 according to FIG. 3 consists substantially of a housing 82 which has a preferably inclined front plate 84.

Said front plate 84 corresponds substantially to the front plate 12 of FIG. 1. Accordingly, in said front plate 84 a groove 86 is again provided which extends from the inlet end 88 to the outlet end 90.

This groove includes a first horizontal branch 92, an adjoining branch 94 bent substantially at a right-angle, a branch 96 which follows the branch 94 and is again bent substantially at a right-angle, a branch 98 following the branch 96 and bent at a right-angle, a branch 100 adjoining the branch 98 and bent substantially at a right-angle and a branch 102 following the branch 100 and bent substantially at a right-angle. The branches 92–100 form an S shape whilst the branch 102 rises at least up to the height of the branch 92.

The branches 92, 96 and 100 and the branches 94, 98 and 102 are disposed substantially parallel to each other. However, the branches 94 and 98 may also assume a substantially semicircular form, i.e. a loop form. The significant point is only that the substantially right-angle transitions of the groove 86 do not buckle the capillary tube 104 to be inserted in said groove and corresponding to the capillary tube 36.

Upstream of said groove 86 is a somewhat enlarged groove 106 in to which a syringe 108 can be inserted. This syringe 108 is advantageously connected to the capillary tube 104 and, filled with plasma, is inserted into said grooves 86 and 106.

This embodiment again includes a settling section denoted by A and extending substantially in the branch 94 and the branch 96.

Disposed in the branch 100 is the measuring section B which corresponds in length to the branch 32 according to FIG. 1.

Concerning the arrangement of the branches 82–102 attention is otherwise drawn to the description of FIG. 1. Thus, the branch 102 again represents a rise section and thus corresponds to the branch 34 of FIG. 1.

A comparison of the two embodiments according to FIGS. 1 and 3 shows that in FIG. 3 the branch 22 is dispensed with and the measuring section has been moved from the branch 24 to the lower branch 100. This relocation depends on the arrangement of the syringe 106 which according to a preferred embodiment can be emptied with a syringe drive 110. Said syringe drive 110 is disposed in the front plate 94 and is in the longitudinal axis of the branch 92.

Concerning the form and shape of the groove 86 and the dimension and material of the tube, attention is drawn to the description regarding FIG. 1.

Again provided in the front plate 84 are 3 detectors 112, 114 and 116, the detector 112 advantageously being provided in the lower end of the branch 98 and the detectors 114 and 116 in the branch 100. Advantageously, these detectors 114–116 are again in the form of light sensors and are inserted in openings provided correspondingly in the branches 98 and 100 and thus do not restrict the insertion of the flexible capillary tube 104. Otherwise, these detectors correspond in construction and arrangement to the detectors 40, 42 and 46 and consequently, attention is again drawn to the description regarding FIG. 1. Preferably, the detector 112 is electronically coupled to the syringe drive and stops said syringe drive as soon as the plasma pumped into the capillary tube 104 has reached the detector 112. Accordingly, the filling operation started on closing the cover 54 according to FIG. 1 is interrupted for a predetermined time during which the plasma is disposed in the branches 94, 96 and 98. Concerning the interruption times, attention is drawn to the description of FIG. 1.

When the plasma contained in the settling section A has been regulated to the desired temperature after this time a tube cutting tool 118 is actuated which is disposed at the branch 92 and severs the capillary tube 104 contained in the groove 86. Because of the severing from the closed syringe 108 the plasma contained in the settling section A can flow on due to gravity and thus moves into the measuring section B.

As explained above, this measuring section B is formed between the detectors 114 and 116 and thus corresponds to the measuring section B of FIG. 1 which is formed between the detectors 40 and 42. Otherwise, the temperature regulation and the measurement of the viscosity also corresponds to the embodiment of FIG. 1 and reference is made to the description thereof.

We claim:

1. Apparatus for measuring the viscosity of fluids comprising:
   an outer housing including a front surface having a groove therein:
   a disposable capillary tube means removably mounted in said groove and including at least one loop, each said loop having two substantially horizontal branches including an upper branch and a lower branch for flowing said fluid under the influence of gravity along a predetermined path; and
   means for measuring the rate of flow of said fluid along said path in one of said horizontal branches.

2. The apparatus of claim 1 wherein said tube means includes at least two loops.

3. The apparatus of claim 1 wherein the measuring means includes two detectors disposed along said upper branch at spaced apart locations for measuring said flow rate.

4. The apparatus of claim 1 wherein the measuring means includes two detectors disposed along said lower branch at spaced apart locations for measuring said flow rate.

5. The apparatus of claims 3 or 4 wherein the interval between the said detectors is about 30–200 mm.

6. The apparatus of any one of claim 1–4 wherein said upper and lower branches are separated by a vertical distance of about 40–160 mm.

7. The apparatus of claim 1 also including a rising branch connected to the downstream end of said lower branch.

8. The apparatus of claim 1 also including a vertically rising branch connected to the downstream end of said upper branch.

9. The apparatus of any one of claims 1–4 also including magnetic closure means disposed downstream of said lower branch, and first sensor means electrically connected to said closure means for controlling said closure means.

10. The apparatus of claim 1 also including a syringe drive mounted on said front surface and second sensor means disposed along said path for actuating said syringe drive.

11. The apparatus of claim 10 also including a cutting tool mounted on said housing and third sensor means for actuating said cutting tool.

12. The apparatus of claim 1 wherein said capillary tube means includes a capillary tube formed of a material selected from the group consisting of polyethylene and polyurethane, having an internal diameter of about 0.5–2 mm and a wall thickness of about 0.2–0.5 mm.

13. The apparatus of claim 1 also including means for heating said front surface to a temperature of about 37° C.

14. The apparatus of claim 7 also including a suction pump, said rising branch including at least one loop having vertically spaced substantially horizontal parallel branches, said suction pump being connected to one of said horizontal parallel branches of said rising loop.

15. The apparatus of claim 14 also including a pair of pressure detectors mounted in said horizontal parallel branches for measuring the pressure of said fluid.

16. The apparatus of claim 15 wherein the vertical distance between said horizontal parallel branches is about 60–140 mm.

17. The apparatus of any one of claims 3 or 4 wherein said detectors are optoelectronic sensors.

18. A flexible disposable capillary tube for a fluid viscosity measuring apparatus, the apparatus having a front surface including a groove therein, comprising:
   a hollow capillary tube, said tube being non-reactive with said fluid, and dimensioned for insertion into said groove on the front surface of said apparatus with substantially no constriction of the internal opening of said tube, the internal diameter of said tube being sized for flowing said fluid through said tube without separating said flow under the surface tension of the internal wall of said tube.

19. The capillary tube of claim 18 wherein said tube has a substantially circular cross-section, and an internal diameter of about 0.5 to about 2 mm.

20. The capillary tube of claim 19 wherein said internal diameter is from about 0.7 to about 1.0 mm.

21. The capillary tube of claim 18 wherein the wall thickness of said tube is about 0.2 to about 0.5 mm.

22. The capillary tube of claim 21 wherein the wall thickness of said tube is about 0.3 to about 4 mm.

23. The capillary tube of claim 18 wherein said tube is a light permeable transparent plastic material.

24. The capillary tube of claim 23 wherein said tube is formed of a material selected from the group consisting of polyurethane and polyethylene, and is substantially free of plasticizers.

25. The flexible tube of claim 18 wherein said tube includes a bead on one end thereof for facilitating insertion of said tube into said groove and filling of the fluid into said tube.

* * * * *